(12) United States Patent
Hage et al.

(10) Patent No.: US 7,575,908 B1
(45) Date of Patent: Aug. 18, 2009

(54) IMMOBILIZATION METHOD FOR PRODUCING ACTIVE $\alpha_1$-ACID GLYCOPROTEIN

(75) Inventors: David S. Hage, Hickman, NE (US); Hai Xuan, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 315 days.

(21) Appl. No.: 11/402,298

(22) Filed: Apr. 11, 2006

Related U.S. Application Data

(60) Provisional application No. 60/672,941, filed on Apr. 19, 2005.

(51) Int. Cl.
*C07K 17/14* (2006.01)
*C12N 11/14* (2006.01)

(52) U.S. Cl. .................. 435/174; 530/395; 530/350

(58) Field of Classification Search ............... 435/174; 530/350, 395
See application file for complete search history.

(56) References Cited

U.S. PATENT DOCUMENTS 5,082,929 A * 1/1992 Ngo et al. ............... 530/391.1

OTHER PUBLICATIONS

Aubry et al., Enantioselective chromatography of the antimalarial agents chloroquine, mefloquine, and enpiroline on a 1 -acid glycoprotein chiral stationary phase: Evidence for a multiple-site chiral recognition mechanism. Chirality 1992, 4, 30-35.
Cogswell, 3rd, et al. Development of a novel probe for measuring drug binding to the F 1 *S variant of human alpha 1-acid glycoprotein, J. Pharm. Sci. 90 (2001) 1407-1423.
Enquist and Hermansson, Separation and quantitation of (R)- and (S)-atenolol in human plasma and urine using an alpha 1-AGP column. Chirality 1989, 1, 209-215.
Fleminger et al., Oriented immobilization of periodate-oxidized monoclonal antibodies on amino and hydrazide derivatives of Eupergit C, Appl. Biochem. Biotechnol. 23 (1990) 123-37.
Gyimesi-Forras et al., New data on the sorption properties of 1-acid glycoprotein chiral stationary phase. Chirality 1999, 11, 212-217.
Gyimesi-Forras et al., Study on the sorption properties of alpha1-acid glycoprotein (AGP)-based stationary phase modified by organic solvents. Chirality 2003, 15, 377-381.
Hage and Austin, High-performance affinity chromatography and immobilized serum albumin as probes for drug- and hormone-protein binding, J. Chromatogr. B 739 (2000) 39-54.
Hage and Tweed, Recent advances in chromatographic and electrophoretic method for the study of drug-protein interactions, J. Chromatogr. B 699 (1997) 499-525.
Hage, Periodate oxidation of antibodies for site-selective immobilization in immunoaffinity chromatography, Method. Mol. Biol. 147(2000) 69-82.
Jewell et al., Alpha 1-acid glycoprotein high-performance liquid chromatography column (EnantioPAC) as a screening tool for protein binding., J. Chromatogr. 487 (1989) 257-64.

Keener et al., Optimization of oxidized antibody labeling with lucifer yellow CH, BioTechniques (1994) 894-7.
Kuroda et al., Role of biantennary glycans and genetic variants of human alphal-acid glycoprotein in enantioselective binding of basic drugs as studied by high performance frontal analysis/capillary electrophoresis, Pharmaceutical research 18(2001) 389-93.
Li and Lloyd, Direct chiral separations by capillary electrophoresis using capillaries packed with an .alpha.1-acid glycoprotein chiral stationary phase Anal. Chem. 1993, 65, 3684-3690.
Locatelli et al., Determination of warfarin enantiomers and hydroxylated metabolites in human blood plasma by liquid chromatography with achiral and chiral separation. J Chromatogr B Analyt Technol Biomed Life Sci. Apr. 25, 2005;818(2):191-8.
Morehead et al., Optimization of oxidation of glycoproteins: an assay for predicting coupling to hydrazide chromatographic supports, J. Chromatogr. 587 (1991) 171-6.
O' Shannessy and Quarles, Labeling of the oligosaccharide moieties of immunoglobulins, J. Immunol. Methods 99 (1987) 153-161.
O' Shannessy and Quarles, Specific conjugation reactions of the oligosaccharide moieties of immunoglobulins, J. Appl. Biochem. 7 (1985) 347-55.
O' Shannessy, Hydrazido-derivatized supports in affinity chromatography, J. Chromatogr. 510 (1990) 13-21.
Ruhn et al., Development of dihydrazide-activated silica supports for high-performance affinity chromatography, J. Chromatogr. A 669 (1994) 9-19.
Schill et al., Chiral separations of cationic and anionic drugs on an alpha 1-acid glycoprotein-bonded stationary phase (EnantioPac). II. Influence of mobile phase additives and pH on chiral resolution and retention. J Chromatogr. Sep. 19, 1986;365:73-88.
Vandenbosch et al., Evaluation of the enantioselectivity towards beta-blocking agents of the alpha1 glycoprotein type chiral stationary phase: Chiral AGP glycoprotein type chiral stationary phase: Chiral AGP, Chromatographia 1992, 33, 454-462.
Wolfe and Hage, Studies on the rate and control of antibody oxidation by periodate, Anal. Biochem. 231 (1995) 123-30.
Xuan and Hage, Evaluation of a hydrazide-linked alpha1-acid glycoprotein chiral stationary phase: separation of R- and S-propranolol. J Sep Sci. Jul. 2006;29(10):1412-22.
Xuan and Hage, Immobilization of alpha(1)-acid glycoprotein for chromatographic studies of drug-protein binding. Anal. Biochem. 2005, 346, 300-310.

* cited by examiner

*Primary Examiner*—Chih-Min Kam
(74) *Attorney, Agent, or Firm*—Thompson Coburn LLP; Charles P. Romano

(57) ABSTRACT

A method and kit for immobilization of a glycoprotein. The method may include activating an affinity support. The affinity support may be activated by reacting the affinity support with a compound that is reactive with one or more functional groups included within the glycoprotein. The method may also include oxidizing the glycoprotein in which oxidation conditions are selected to yield an oxidized glycoprotein that is biologically active and contains a sufficient number of reactive aldehyde groups for coupling to a support. For example, the oxidized glycoprotein may include five reactive aldehyde groups. In addition, the method may include reacting the oxidized-glycoprotein with the activated affinity support to immobilize the glycoprotein.

13 Claims, 4 Drawing Sheets

IMMOBILIZATION METHOD FOR PRODUCING ACTIVE $\alpha_1$-ACID GLYCOPROTEIN

CROSS REFERENCE TO RELATED APPLICATIONS

The present application claims the benefit under 35 U.S.C. § 119(e) of U.S. Provisional Patent Application Ser. No. 60/672,941, entitled "Immobilization Method for Producing Active Alpha 1-Acid Glycoprotein," filed Apr. 19, 2005 which is herein incorporated by reference in its entirety.

STATEMENT REGARDING FEDERALLY SPONSORED RESEARCH OR DEVELOPMENT

This invention was made with government support under GM044931 awarded by the National Institute of Health. The government has certain rights in the invention.

FIELD OF THE INVENTION

The present invention relates generally to the field of protein immobilization, and particularly to an immobilization method for producing active $\alpha_1$-acid glycoprotein.

BACKGROUND OF THE INVENTION

The binding of serum proteins with drugs has long been of interest since it affects the transportation and distribution of pharmaceutical agents in the body. One serum protein that is often involved in this process is $\alpha_1$-acid glycoprotein (AGP). This protein has a carbohydrate content of 45% (w/w). The mean molecular mass for its native form is approximately 41,000 g/mol. AGP has a single polypeptide chain with up to five carbohydrate moieties. It has been estimated that there are 12-20 different forms of AGP in serum due to variations in its amino acid sequence and the types and numbers of carbohydrate groups attached to its polypeptide chain.

Although the exact biological function of AGP is still not clear, the binding of drugs to AGP has long been of interest since this may affect the transport and distribution of such agents in the body. This binding occurs primarily with basic and neutral solutes and is thought to mainly involve hydrophobic interactions; however, coulombic interactions, hydrogen bonding and steric effects may also be present.

Various techniques have been previously used to examine the binding of drugs to AGP. Examples include equilibrium dialysis, ultrafiltration, capillary electrophoresis and various spectroscopic methods. Recent reports with AGP or other serum proteins like human serum albumin (HSA) have also explored the use of high performance affinity chromatography (HPAC) and surface plasmon resonance biosensors for studying the binding of these proteins with drugs. Advantages of these later techniques versus traditional solution-phase methods include their improved precision, their ease of automation, the convenience with which they can provide equilibrium and kinetic information on drug-protein binding, and their ability to reuse the same protein preparation for hundreds of samples.

One desirable feature in the immobilization of a protein for binding studies is to have the protein in a final form that closely mimics the behavior of its native form. It has been demonstrated in many studies based on HPAC that immobilized HSA closely mimics the binding of drugs to the soluble form of this protein. However, previous studies with immobilized AGP have been successful. For instance, reports in which AGP has been immobilized through ionic immobilization and cross-linking have produced materials with a poor correlation versus the behavior of soluble AGP. In addition, no successful reports using currently available commercial AGP columns for drug-protein binding studies have yet been reported, despite the widespread use of such columns for chiral separations.

Therefore, it would be desirable to provide a method of AGP immobilization which produces immobilized AGP which closely mimics the behavior of AGP in its native form.

SUMMARY OF THE INVENTION

Accordingly, the present invention provides a method for the immobilization of AGP based on the mild oxidation of AGP to generate aldehyde groups in its carbohydrate regions. This oxidized form of AGP will then be reacted with a hydrazide-activated support. The behavior of immobilized AGP that is produced by this method is evaluated by using it in HPLC columns to examine the binding to R- and S-propranolol, two solutes that have relatively well-characterized interactions with soluble AGP. The binding of the resulting immobilized AGP to other drugs is also determined.

In a first aspect of the present invention, a method for immobilization of a glycoprotein. In an embodiment, the method may include activating an affinity support. The affinity support may be activated by reacting the affinity support with a compound that is reactive with one or more functional groups included with the glycoprotein. The method may also include oxidizing the glycoprotein in which oxidation conditions are selected to yield an oxidized glycoprotein that is biologically active and includes a sufficient number of reactive aldehyde groups for coupling to a support. For example, the oxidized glycoprotein may include five reactive aldehyde groups. In addition, the method may include reacting the oxidized-glycoprotein with the activated affinity support to immobilize the glycoprotein.

In accordance with a further aspect of the present invention, a glycoprotein immobilization kit is provided. In such aspect, the kit may include an affinity support for immobilizing the glycoprotein. Further, an activating solution for activating the affinity support so that the support is reactive with one or more functional groups within the glycoprotein may be included. For instance, the activating solution may include a hyrazide-containing agent. In addition, the kit may include an oxidizing solution for oxidizing the glycoprotein. In an aspect, the oxidizing solution is of a composition that yields an oxidized glycoprotein that is biologically active and contains a sufficient number of reactive aldehyde groups (e.g., at least five reactive aldehyde groups) for coupling to a support. Reacting the oxidized-glycoprotein to the activated affinity support.

In accordance with an additional aspect of the present invention, a solid support for use in a chiral separation assay is provided. The solid support may have an hydrazide-activated surface which is reactive with one or more functional groups of an oxidized alpha one ($\alpha_1$) acid glycoprotein. For instance, the oxidized-glycoprotein may include at least five reactive aldehyde groups. The oxidized glycoprotein may be reacted with the hydrazide-activated support surface to immobilize the glycoprotein by linking the oxidized-glycoprotein to the hydrazide-activated support. Such reaction forms a hydrazide-linked alpha one ($\alpha_1$) acid glycoprotein complex capable of separating a chiral drug.

It is to be understood that both the foregoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the presently preferred embodiments of the invention, examples of which are illustrated in the accompanying drawings.

Figure 1:
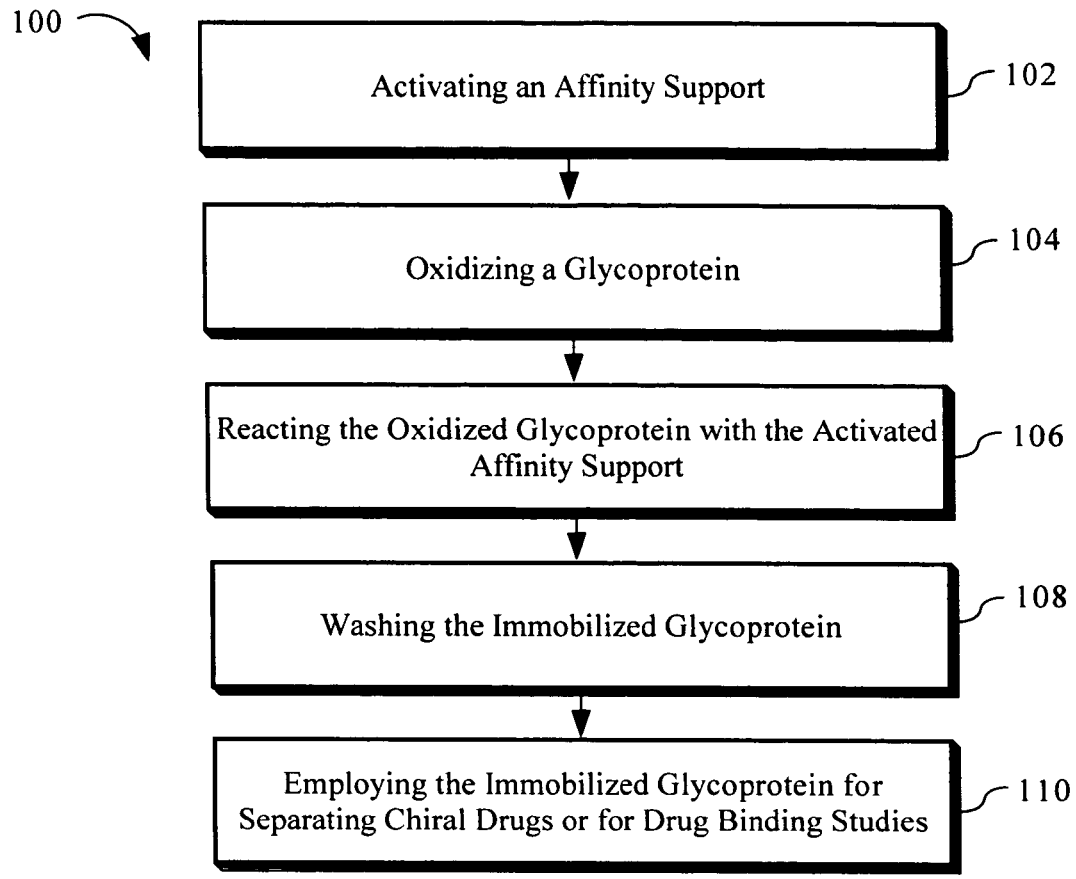
FIG. 1 is a flow chart illustration of a method of immobilization of a glycoprotein in accordance with an exemplary embodiment of the present invention.

Referring to FIG. 1, a method 100 for immobilization of a glycoprotein is provided. In an exemplary embodiment, the method 100 may include activating an affinity support 102. In such embodiment, the affinity support may be activated by reacting the affinity support with a compound that is reactive with one or more functional groups included within the glycoprotein. For instance, for alpha one ($\alpha_1$) acid glycoprotein the affinity support may be activated with hydrazide, amine, and other like related agents. In addition, the activated silica support may be employed to immobilize a glycoprotein such as $\alpha_1$-acid glycoprotein.

In further embodiments, the method 100 may include oxidizing the glycoprotein 104. In an exemplary embodiment, oxidation conditions are selected to maximize the activity of the glycoprotein after oxidation. For example, in order to maximize the activity of $\alpha_1$-acid glycoprotein, conditions were chosen such that excessive damage to the carbohydrate chains or amino acids within $\alpha_1$-acid glycoprotein's structure did not occur. Further, the oxidation conditions were chosen so that a sufficient number of aldehyde groups (e.g., at least five) were present to couple $\alpha_1$-acid glycoprotein to an activated support. In an embodiment, oxidation conditions may include reacting the glycoprotein such as $\alpha_1$-acid glycoprotein with the oxidizing reagent periodate or by using comparable oxidative procedures. It is contemplated that periodate concentrations may range from 0.01 mM to 50 mM, and preferably from 5 mM to 20 mM.

The method 100 may also include reacting the oxidized-glycoprotein with the activated affinity support 106 to immobilize the glycoprotein by linking the oxidized-glycoprotein to the activated affinity support. In addition, the immobilized glycoprotein may be washed 108 following reacting the oxidized glycoprotein with the activated affinity support to remove remaining non-reacted compound. Moreover, the method 100 may include employing the immobilized glycoprotein for separating chiral drugs 110 such as propranolol and other like related compounds.

In accordance with a further embodiment of the present invention, a glycoprotein immobilization kit is provided. In an exemplary embodiment, the kit may include an affinity support for immobilizing the glycoprotein. Further, an activating solution for activating the affinity support so that the support is reactive with one or more functional groups within the glycoprotein may be included. For instance, the activating solution includes a reagent such as hydrazide, amine, and other like compounds.

In further exemplary embodiments, the kit may include an oxidizing solution for oxidizing the glycoprotein. In an embodiment, the oxidizing solution is of a composition that yields an oxidized glycoprotein that is biologically active and contains a sufficient number of reactive aldehyde groups (e.g., at least five reactive aldehyde groups) for coupling to a support. For example, the oxidizing solution may include oxidation conditions may include the oxidizing reagent periodate. It is contemplated that periodate concentrations may range from 0.01 mM to 50 mM, and preferably from 5 mM to 20 mM. In an alternative embodiment, the oxidizing solution includes approximately 20 mM sodium acetate and approximately 0.15 mM sodium chloride in a one to one volume to volume ratio with periodate concentrations ranging from 5 mM to 20 mM. The kit may also include a washing solution for washing the activated affinity support following reacting the oxidized glycoprotein with the activated affinity support to remove remaining non-reacted compound on the affinity support. For example, the washing solution may include In an additional exemplary embodiment, a solid support for use in a chiral separation assay is disclosed. In an embodiment, the solid support may have an activated surface including hydrazide or amine groups, or other like activated surfaces. In the embodiment, the hydrazide-activated surface may be reactive with one or more functional groups of an oxidized glycoprotein such as $\alpha_1$-acid glycoprotein. For instance, this may be obtained through the use of approximately five aldehyde groups in active $\alpha_1$-acid glycoprotein, such as is produced by oxidizing $\alpha_1$-acid glycoprotein with 5 to 20 mM periodate for 10 minutes at pH 7.0 and 4° C. Reacting the oxidized glycoprotein with the activated support surface immobilizes the glycoprotein by linking the oxidized-glycoprotein to the activated support. As such, a hydrazide-linked glycoprotein complex capable of separating a chiral drug (e.g., propanolol and like compounds) is formed.

Some of the specific examples in accordance with exemplary embodiments of the present invention are provided below. Further, additional examples in accordance with the present invention may be found in the publication entitled "Immobilization of $\alpha_1$-acid glycoprotein for chromatographic studies of drug-protein binding", Analytical Biochemistry, Volume 346, 2005, pages 300 to 310 by Hai Xuan and David S. Hage, which is herein incorporated by reference in its entirety.

EXAMPLE 1

Preparation of Oxidized $\alpha_1$-acid Glycoprotein

Figure 2A:
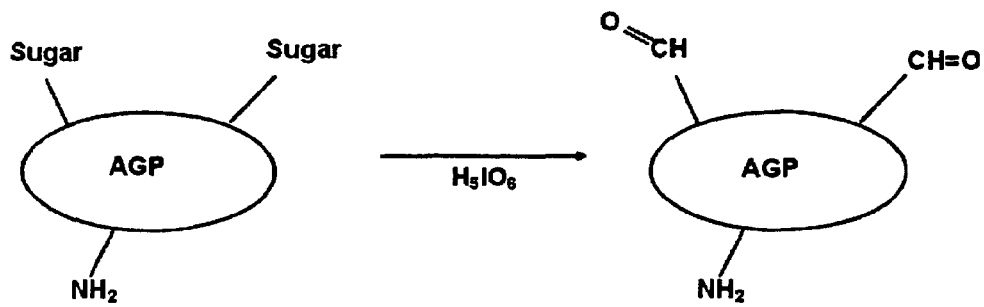
FIG. 2A is a schematic illustration of the oxidation of $\alpha_1$-acid glycoprotein by periodate acid in accordance with an exemplary embodiment of the present invention.

FIG. 2A illustrates an exemplary method for preparing oxidized $\alpha_1$-acid glycoprotein. The conditions chosen for this reaction vary according to the final degree of oxidation desired. For instance, 2 to 5 milligram (mg)/milliliter (mL) $\alpha_1$-acid glycoprotein was dissolved in pH 7.0, 20 mM sodium acetate and 0.15 M sodium chloride and combined in a 1:1 (v/v) ratio with 5-20 mM periodic acid in the same buffer. In such example, $\alpha_1$-acid glycoprotein had a purity of at least 99.0% and was prepared from a pooled serum sample that included approximately 44% of the F variant of AGP, 29% of the S variant and 27% of the A variant. This mixture was allowed to react for 10 to 15 minutes at room temperature in the dark and quenched by adding 0.25 mL ethylene glycol per milliliter of sample. After this new mixture had reacted for 2 minutes, it was put into a dialysis bag at 4° C. for 2 hours against 2 liters pH 7.0, 20 mM acetate buffer containing 0.15 M sodium chloride. This was followed by three additional two-hour dialysis cycles against 2 liter portions of pH 7.0, 0.10 M potassium phosphate buffer.

EXAMPLE 2

Analysis of Oxidized $\alpha_1$-acid Glycoprotein

The extent of $\alpha_1$-acid glycoprotein oxidation produced by following the procedures described in Example 1 was monitored using Lucifer yellow (LyCH) as a labeling agent. In this technique, a 3 mg/mL solution of LyCH in pH 6.5, 0.10 M phosphate buffer was mixed with an equal portion of an oxidized $\alpha_1$-acid glycoprotein solution prepared in Example 1 and allowed to react for 2 hours. This mixture was then applied to a 10 mL Econo-Pac 10DG column (Bio-Rad Laboratories) to remove the excess LyCH using pH 7.0, 0.10 M phosphate buffer as the mobile phase. The labeled AGP was then collected and dialyzed for several hours at 4° C. against two to three 2 L portions of pH 7.4, 0.10 M phosphate buffer.

The amount of LyCH per $\alpha_1$-acid glycoprotein in the labeled sample was determined by using a manual absorbance method. To do this, calibration curves were first constructed at 280 nm for 0-2 mg/mL $\alpha_1$-acid glycoprotein and at both 280 and 428 nm for 0-3 mg/mL LyCH in pH 7.4, 0.10 M phosphate buffer (Note: $\alpha_1$-acid glycoprotein has no measurable absorbance at 428 nm). These curves gave linear relationships with a molar absorptivity of 2.91 ($\pm$0.02)$\times 10^4$ $M^{-1}$ $cm^{-1}$ for $\alpha_1$-acid glycoprotein at 280 nm and molar absorptivities for LyCH of 2.62 ($\pm$0.08)$\times 10^4$ $M^{-1}$ $cm^{-1}$ at 280 nm and 1.27 ($\pm$0.05)$\times 10^4$ $M^{-1}$ $cm^{-1}$ at 428 nm.

For the analysis of LyCH-labeled $\alpha_1$-acid glycoprotein, the LyCH concentration in each sample was determined by using the sample's absorbance at 428 nm. The measured LyCH concentration was then used along with the known molar absorptivity of LyCH at 280 nm to calculate the absorbance for LyCH at 280 nm in the labeled sample. This absorbance was then subtracted from the total absorbance measured for the sample at this wavelength and used to determine the concentration of $\alpha_1$-acid glycoprotein. These results were combined to give the LyCH/$\alpha_1$-acid glycoprotein ratio for the sample, which provided a measure of number of aldehydes available on the oxidized $\alpha_1$-acid glycoprotein for coupling to hydrazide groups.

EXAMPLE 3

Immobilization of Oxidized $\alpha_1$-acid Glycoprotein

Figure 2B:
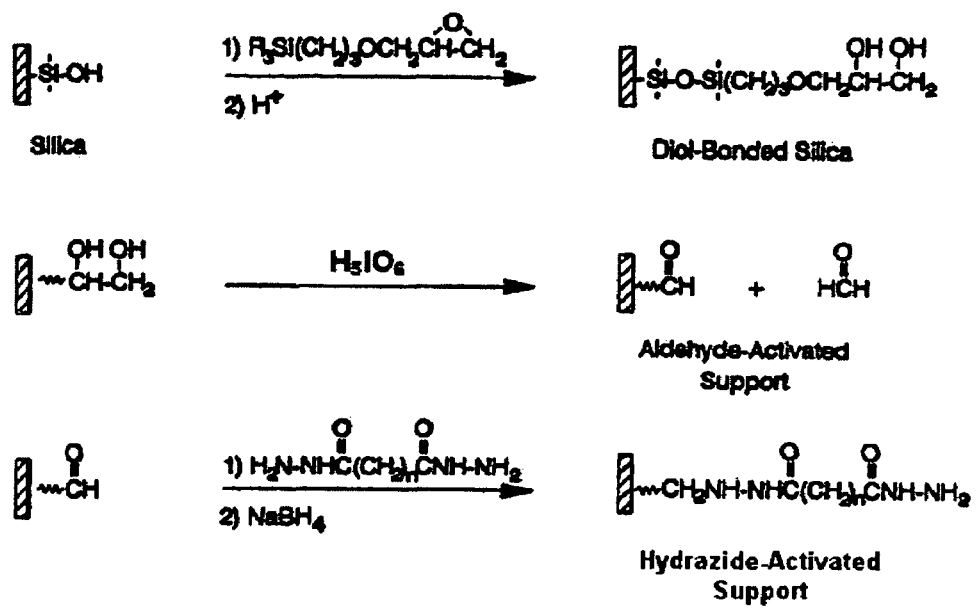
FIG. 2B is a schematic illustration of the preparation of hydrazide-activated silica in accordance with an exemplary embodiment of the present invention.

First, hydrazide-activated silica was prepared as shown in FIG. 2B. For example, 1 g of Nucleosil Si-300 obtained from Alltech (Deerfield, Ill.) was placed in 8.5 mL of pH 5.5, 0.1 M sodium acetate buffer and degassed by sonication under vacuum for 10 to 15 minutes. Next, 0.20 mL of 3-glycidoxypropyltrimethoxysilane was added and the solution was shaken for 5 hours at 90° C. The epoxy silica formed by this reaction was washed several times with water and a pH 3.0 sulfuric acid solution. This support was next suspended in a pH 3.0 sulfuric acid solution (using 100 mL of this solution per gram of silica) and refluxed for 90 minutes. The diol-bonded silica formed as the product was washed with several portions of water, methanol, and ether and dried overnight under vacuum at room temperature. To make dihydrazide-activated silica, 1 g of the diol-bonded silica was suspended in 20 mL of a 90% (v/v) acetic acid-water mixture containing 1 g periodic acid. This mixture was sonicated under reduced pressure for 10 to 15 minutes and shaken for 2 hours at room temperature. The resulting aldehyde silica was washed four times with deionized water or pH 7.0, 0.1 M phosphate buffer to remove any excess periodic acid. To this aldehyde silica was then added 50 mL of pH 7.0, 0.1 M phosphate buffer containing 0.13 g oxalic dihydrazide. This mixture was shaken for 1 to 2 hours, centrifuged and washed four times with pH 7.0, 0.1 M phosphate buffer. After activation, the remaining aldehyde groups were reduced by adding 0.2 g sodium borohydride in 20 mL of pH 8.0, 0.1 M phosphate buffer. This mixture was shaken for 90 minutes and washed four times with water. The hydrazide silica was stored under vacuum at room temperature or in the pH 7.0 phosphate buffer at 4° C.

Figure 2C:
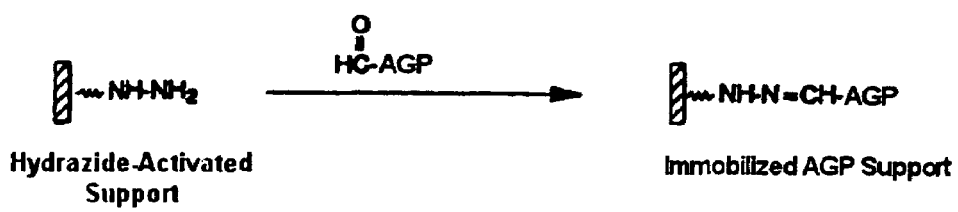
FIG. 2C is a schematic illustration of the immobilization of $\alpha_1$-acid glycoprotein to a hydrazide-activated support in accordance with an exemplary embodiment of the present invention.

Oxidized $\alpha_1$-acid glycoprotein was immobilized to hydrazide-activated silica by a procedure illustrated in FIG. 2C. In exemplary studies, a 5 mL portion of pH 7.0, 0.10 M phosphate buffer containing 1.5 mg/mL oxidized $\alpha_1$-acid glycoprotein was mixed with 0.03 grams of hydrazide-activated silica. This mixture was sonicated under aspirator vacuum for 10 minutes to remove any air bubbles from the suspension. It was then placed onto a shaker and allowed to react at 4° C. for up to seven days, with more than two days being optimum. The reaction was stopped by centrifuging the reaction mixture and removing the supernatant. The support was next washed several times with pH 7.0, 0.10 M phosphate buffer, followed by several additional washings with deionized water. Any hydrazide groups remaining on this support were removed by adding a 200-fold excess of glyceraldehyde versus the support's original hydrazide content. This mixture was shaken at 4° C. for 6 hours. The support was then washed several times with pH 7.0, 0.10 M phosphate buffer. The amount of immobilized $\alpha_1$-acid glycoprotein was determined by comparing the final and initial concentrations of $\alpha_1$-acid glycoprotein in the reaction slurry, using absorbance measurements at 280 nm.

EXAMPLE 4

Chromatographic Studies with R- and S-Propranolol

The $\alpha_1$-acid glycoprotein and hydrazide-activated supports were downward slurry-packed at 28 MPa (4000 psi) into 50×4.1 mm I.D. stainless steel columns. These columns were enclosed in water jackets for temperature control. All studies, except those examining the temperature dependence of propranolol—$\alpha_1$-acid glycoprotein binding, were performed at 37° C. The mobile phases and packing solutions were prepared using pH 7.4 phosphate buffered saline (PBS, composition: 0.013 M potassium dihydrogen phosphate, 0.053 M disodium hydrogen phosphate and 0.133 M sodium chloride). Prior to use, all mobile phases were filtered through a 0.45 μm cellulose acetate filter and degassed under vacuum for 10 min. Elution of R- and S-propranolol was detected by monitoring the absorbance at 225 nm. Zonal elution studies were performed on the $\alpha_1$-acid glycoprotein column by applying pH 7.4 phosphate buffer solution containing up to 20 μM of the desired competing agent while making 20 μL injections of R-propranolol or S-propranolol onto the column. At each concentration of competing agent, three replicate injections of the desired analyte were made. The propranolol samples were prepared by dissolving 5.0 μM R- or S-propranolol in the appropriate mobile phase. All mobile phases containing propranolol were prepared using the individual enantiomers or propranolol. The flow rate ranged from 0.8 to 1.5 mL/min, with no significant changes in the retention factors being noted under this range of conditions. There was also no observed change in retention with small variations in the amount of injected propranolol, indicating that linear elution conditions were present during these experiments.

The retention times for propranolol were calculated using a $B/A_{0.5}$ method. The column void volume was determined by making injections of sodium nitrate onto a column containing only hydrazide-activated silica while monitoring the absorbance at 205 nm. All elution times were corrected for the extra-column volume of the chromatographic system, as determined by making injections of R-propranolol or S-propranolol when no column was present. A correction for the small amount of non-specific binding between propranolol and the hydrazide support was made by measuring the retention factors for this drug on a column equivalent in size to the $\alpha_1$-acid glycoprotein column, but containing only hydrazide-activated silica. This was measured at each propranolol concentration in the mobile phase and accounted for 3-15% of the retention factors noted for propranolol on the $\alpha_1$-acid glycoprotein column. The $\alpha_1$-acid glycoprotein columns were found to be stable over at least three months, with only a 5% change in retention being noted over the course of 50 injections and the application of 4000 column volumes of the mobile phase. The column was stored in pH 7.4 PBS buffer at 4° C. when not in use.

The effects of oxidation on $\alpha_1$-acid glycoprotein are presented in Table 1, below. All of the results presented in Table 1 were determined at 37° C. in pH 7.4 phosphate buffered saline. The numbers in parentheses represent a range of ± one standard deviation.

| Measured property | Periodate conc. used for AGP oxidation | | |
|---|---|---|---|
| | 10 mM | 20 mM | 50 mM |
| AGP immobilized (mg/g silica) | 10.2 (±0.2) | 15.8 (±0.4) | 14.5 (±0.5) |
| Binding capacity (mg/g silica) | 6.8 (±0.2) | 6.3 (±0.3) | 6.8 (±0.3) |
| Specific activity (mg/mg AGP) | 0.67 (±0.02) | 0.40 (±0.02) | 0.47 (±0.03) |
| Association constant ($\times 10^{-6} M^{-1}$) | 3.1 (±0.2) | 3.0 (±0.3) | 0.95 (±0.05) |

The effect of temperature on the binding of R- and S-propranolol to $\alpha_1$-acid glycoprotein columns is presented in Table 2, below. All of the results presented in Table 2 were generated by performing self-competition zonal elution studies at temperatures ranging from 5° C. to 37° C. in pH 7.4 phosphate buffered saline. The numbers in parentheses represent a range of ± one standard deviation.

| Analyte | Association equilibrium constant, $K_a$ ($M^{-1}$) | | | |
|---|---|---|---|---|
| | 37° C. | 25° C. | 15° C. | 5° C. |
| S-Propranolol | 4.2 (±0.3) × $10^6$ | 5.2 (±1.7) × $10^6$ | 9 (±2) × $10^6$ | 11 (±3) × $10^6$ |
| R-Propranolol | 2.7 (±0.2) × $10^6$ | 3.9 (±0.2) × $10^6$ | 7 (±1) × $10^6$ | 8 (±2) × $10^6$ |

The effect of other separation conditions such as pH were also evaluated. For instance, as the pH decreased from 7.4 to 4.8, the retention factor for R-propranolol decreased from 132 to 17.8 (87%), while the retention factor for S-propranolol decreased from 167 to 17.8 (89%). This pH dependent behavior indicates that the immobilized $\alpha_1$-acid glycoprotein is mimicking the behavior of such protein in solution.

EXAMPLE 5

Drug Screening on $\alpha_1$-acid Glycoprotein Column

The binding of other drugs to the $\alpha_1$-acid glycoprotein columns were examined at 25 or 37° C. using pH 7.4, 0.067 M potassium phosphate buffer. These drugs were selected based on their binding to soluble $\alpha_1$-acid glycoprotein. Samples of each drug were prepared at a concentration of 5 mM. The injection volume for each sample was 25 μL, with all samples being examined in triplicate. The detection wavelengths were as follows: imipramine, 210 nm; pindolol, 216 nm; trifluoperazine, 257 nm; and epinephrine and isoproterenol, 203 nm. All other drugs were monitored at 225 nm. All samples were used within one day of preparation. The present conditions yielded a more effective approach for the immobilization of $\alpha_1$-acid glycoprotein with perphenzaine, triflupromazine, quinidine, and lidocaine when compared to previously reported findings. Further, the presently employed immobilization method gave better performance than thiol-based immobilization in work with $\alpha_1$-acid glycoprotein and other compounds (e.g., pindolol, quinidine, and propranolol).

Figure 3:
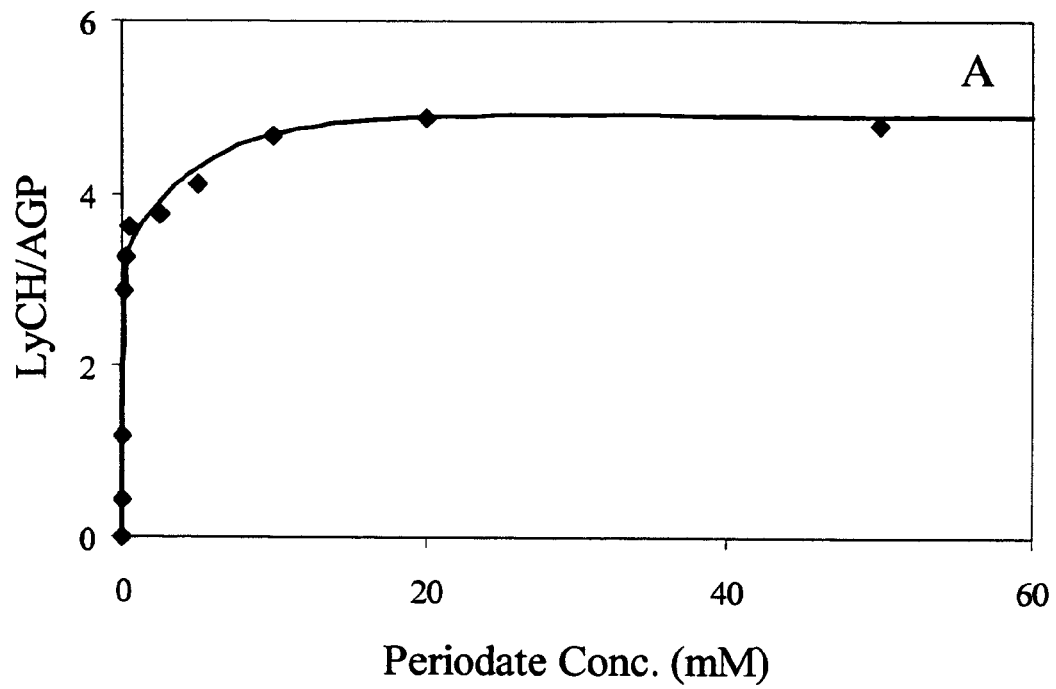
FIG. 3A is a schematic illustration of the degree of $\alpha_1$-acid glycoprotein oxidation at various periodate concentrations in accordance with an exemplary embodiment of the present invention, wherein the ratio of Lucifer yellow per $\alpha_1$-acid glycoprotein (LyCH/AGP) is a measure of the number of aldehyde groups that are available for coupling on $\alpha_1$-acid glycoprotein.
FIG. 3B is a schematic illustration of the degree of $\alpha_1$-acid glycoprotein immobilized to hydrazide-actiated silica after oxidation at various periodate concentrations in accordance with an exemplary embodiment of the present invention.
Figure 3:
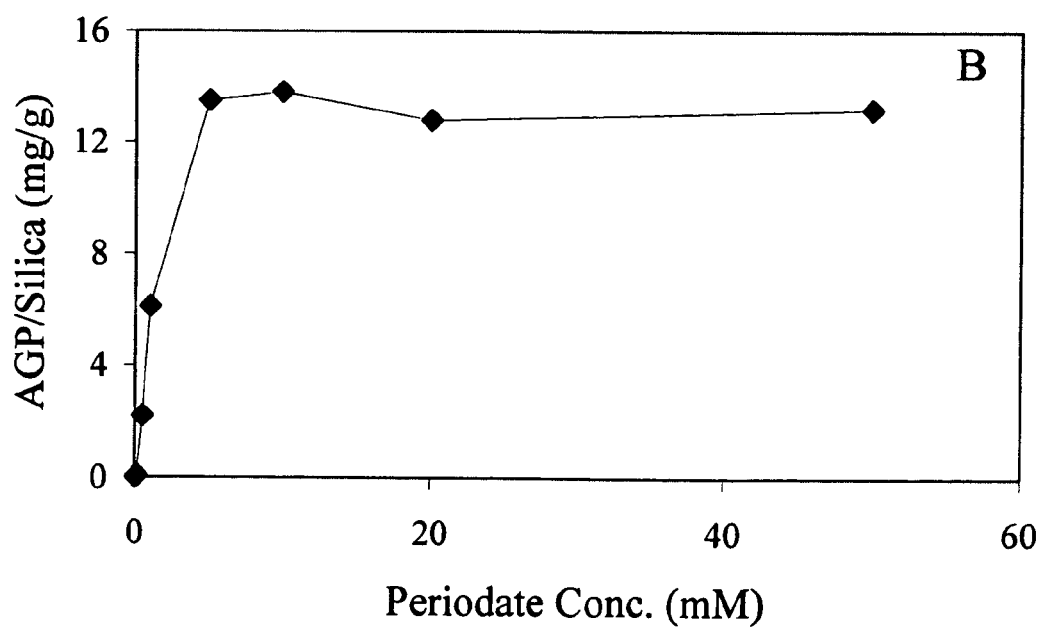

Referring to FIG. 3A, the degree of $\alpha_1$-acid glycoprotein oxidation at various periodate concentrations in accordance with Example 3 of the present invention is provided. In the present Example, reactions occurred over a 10 minute time period at 4° C. in pH 7.0 buffer including 20 mM sodium acetate and 0.15 M sodium chloride. As illustrated in FIG. 3A, an increase in the amount of Lucifer yellow (LyCH) per $\alpha_1$-acid glycoprotein (LyCH/AGP) occurred as the concentration of periodate increased from 0 mM and 0.5 mM. Further, a plateau in the LyCH/AGP ratio was observed between 10 mM and 50 mM. The LyCH/AGP ratio observed under these conditions indicates that there were up to five usable aldehyde groups generated per $\alpha_1$-acid glycoprotein molecule. It is contemplated that the aldehyde groups are located in the terminal sialic acid regions with the glycoprotein's carbohydrate chain since such regions are known to be the most susceptible of periodate oxidation under the presently employed conditions.

Referring to FIG. 3B, the degree of $\alpha_1$-acid immobilized to hydrazide-actiated silica after oxidation at various periodate concentrations in accordance with Example 3 of the present invention is illustrated. As illustrated in FIG. 3B, at 0.05 mM periodate there was no significant amount of $\alpha_1$-acid glycoprotein immobilized even though it was known that such conditions gave about one reactive aldehyde group per $\alpha_1$-acid glycoprotein. However, an increase in the amount of immobilized $\alpha_1$-acid glycoprotein was observed with an increase in periodate concentration, particularly in the range of 0.05 mM to 5 mM periodate. This value reached 13.8 milligrams of $\alpha_1$-acid glycoprotein per gram silica when 5 mM periodate was used, with similar values being observed for periodate concentrations up to 50 mM. As illustrated in FIG. 3A, this is the same range of conditions that gave rise to five reactive aldehydes per $\alpha_1$-acid glycoprotein.

It is contemplated that $\alpha_1$-acid glycoprotein containing fewer than five aldehyde groups was unable to be immobilized effectively to the hydrazide-activated support due to steric hindrance, where many of these aldehydes groups may not have been able to come in contact with the support's surface. Thus, based upon the present experimental findings, a preferred embodiment involves oxidizing $\alpha_1$-acid glycoprotein by reacting 5-20 mM periodate (typically 10 mM for optimum reproducibility) for 10 min at 4° C. with 5.0 mg/mL $\alpha_1$-acid glycoprotein in a pH 7.0 buffer containing 20 mM sodium acetate and 0.15 M sodium chloride.

Figure 4:
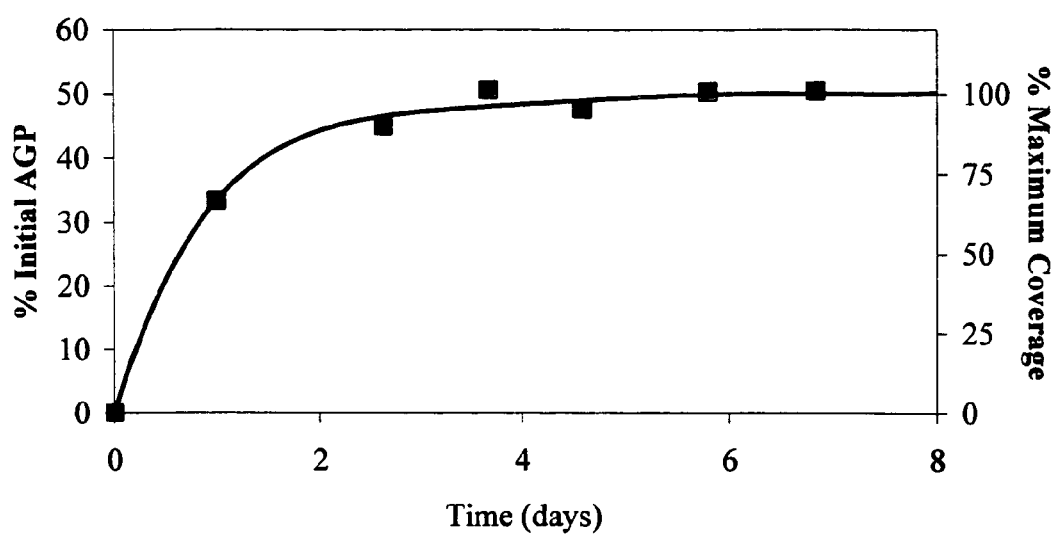
FIG. 4 is a schematic illustration of the rate of immobilization for oxidized $\alpha_1$-acid glycoprotein in accordance with an exemplary embodiment of the present invention, wherein oxidized $\alpha_1$-acid glycoprotein was oxidized with 20 mM periodate for 10 minutes at room temperature before immobilization.

Referring to FIG. 4, rate of immobilization for oxidized $\alpha_1$-acid glycoprotein in accordance with an exemplary embodiment of the present invention in which oxidized $\alpha_1$-acid glycoprotein was oxidized with 20 mM periodate for 10 minutes at room temperature before immobilization. As illustrated in FIG. 4, approximately two-thirds of the maximum amount of immobilized $\alpha_1$-acid glycoprotein was obtained within 24 hours, with over ninety percent of maximum coverage being achieved within approximately two days. Further, longer coupling times did not result in significant change. Under such conditions, thirty-three percent of the added $\alpha_1$-acid glycoprotein was immobilized in 24 hours with half remaining in solution after the immobilization had reached completion. Therefore, the present conditions appeared to be adequate to saturate the available coupling sites on the support.

It is believed that the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. Further, it is to be understood that the claims included below are merely exemplary of the present invention and are not intended to limit the scope of coverage which has been enabled by the written description.

What is claimed is:

1. A method for immobilization of an alpha one ($\alpha_1$) acid glycoprotein, comprising:
   activating an affinity support, the affinity support being activated by reacting the affinity support with a compound that is reactive with one or more functional groups including within the one ($\alpha_1$) acid glycoprotein;
   oxidizing the alpha one ($\alpha_1$) acid glycoprotein, oxidation conditions being selected to i) yield an oxidized alpha one ($\alpha_1$) acid glycoprotein that includes at least five reactive aldehyde groups and ii) maximize activity of said alpha one ($\alpha_1$) acid glycoprotein after oxidation, wherein said oxidation conditions comprise reacting the alpha one ($\alpha_1$) acid glycoprotein with 5 mM to 20 mM periodate for about 10 to 15 minutes;
   reacting the oxidized alpha one ($\alpha_1$) acid glycoprotein with the activated affinity support to immobilize the alpha one ($\alpha_1$) acid glycoprotein by linking the oxidized alpha one ($\alpha_1$) acid glycoprotein to the activated affinity support.

2. The method as claimed in claim 1, wherein the oxidized alpha one ($\alpha_1$) acid glycoprotein includes five reactive aldehyde groups.

3. The method as claimed in claim 1, wherein the activated affinity support is a hydrazide-activated support.

4. The method as claimed in claim 1, wherein the activated affinity support is an amine-activated support.

5. The method as claimed in claim 1, further comprising washing the immobilized alpha one ($\alpha_1$) acid glycoprotein following reacting the oxidized alpha one ($\alpha_1$) acid glycoprotein with the activated affinity support to remove remaining non-reacting alpha one ($\alpha_1$) acid glycoprotein.

6. The method as claimed in claim 1, wherein oxidation conditions include reacting the alpha one ($\alpha_1$) acid glycoprotein with 5 mM to 20 mM periodate at room temperature.

7. The method as claimed in claim 1, wherein the oxidation conditions include reacting the alpha one ($\alpha_1$) acid glycoprotein with 5 mM to 20 mM periodate at about 4° C.

8. The method as claimed in claim 1, wherein the activated affinity support is a hydrazide-activated silica support.

9. The method as claimed in claim 1, further comprising employing the immobilized alpha one ($\alpha_1$) acid glycoprotein for separating chiral drugs.

10. The method as claimed in claim 9, wherein chiral drugs include propranolol.

11. The method of claim 1, wherein said oxidation conditions comprise reacting said alpha one ($\alpha_1$) acid glycoprotein at a concentration of about 2 to 5 milligram/milliliter.

12. The method of claim 1, wherein said oxidation conditions comprise reacting said alpha one ($\alpha_1$) acid glycoprotein at about pH 7.0.

13. The method of claim 1, wherein said oxidation conditions comprise reacting said alpha one ($\alpha_1$) acid glycoprotein at about pH 7.0 for about 10 minutes at about 4° C.

* * * * *